United States Patent [19]

Delmore et al.

[11] Patent Number: 5,654,031
[45] Date of Patent: Aug. 5, 1997

[54] WEB COATING APPARATUS

[75] Inventors: Michael D. Delmore, Mounds View, Minn.; Gary W. Maier, Warren Township, St. Croix County, Wis.; Paul G. Kowski, St. Croix Beach; Rodney W. Hauschulz, Minnetonka, both of Minn.

[73] Assignee: Minnesota Mining and Manufacturing Company, St. Paul, Minn.

[21] Appl. No.: 471,979

[22] Filed: Jun. 6, 1995

Related U.S. Application Data

[63] Continuation of Ser. No. 301,258, Sep. 6, 1994, Pat. No. 5,501,738.

[51] Int. Cl.$^6$ .............................. B65H 18/00; B05D 1/02; B05D 1/40
[52] U.S. Cl. ................. 427/8; 427/177; 427/179; 118/709; 118/62; 118/323; 118/325; 242/532.2; 156/444; 156/446; 156/459
[58] Field of Search .................. 118/674, 681, 118/683, 709, 712, 35, 40, 62, 68, 235, 323, 325, 410, 419, 416; 242/418, 418.1, 412.1, 412.2, 527.2, 532.2; 156/361, 443, 444, 446, 459, 510, 543, 547, 270, 289; 427/177, 179, 8, 290, 356

[56] References Cited

U.S. PATENT DOCUMENTS

| | | | |
|---|---|---|---|
| 2,690,206 | 9/1954 | Mueller | 154/1 |
| 3,121,018 | 2/1964 | Wood, Jr. et al. | 117/4 |
| 3,511,729 | 5/1970 | Williams | 156/154 |
| 3,589,331 | 6/1971 | Westervelt et al. | 118/62 |
| 3,704,835 | 12/1972 | Harley | 242/56 A |
| 3,832,213 | 8/1974 | Brenner | 117/44 |
| 3,929,097 | 12/1975 | Kanda et al. | 118/62 |
| 4,068,614 | 1/1978 | Kopachkov | 118/6 |
| 4,068,615 | 1/1978 | LeNir | 118/6 |
| 4,388,349 | 6/1983 | Korpman et al. | 427/208.4 |
| 4,484,574 | 11/1984 | DeRusha et al. | 128/156 |
| 4,502,479 | 3/1985 | Garwood et al. | 128/90 |
| 4,528,056 | 7/1985 | Hunt et al. | 156/253 |
| 4,570,622 | 2/1986 | von Bonin et al. | 128/90 |
| 4,609,578 | 9/1986 | Reed | 428/76 |
| 4,667,661 | 5/1987 | Scholz et al. | 128/90 |
| 4,690,349 | 9/1987 | Yamaguchi et al. | 242/75.5 |
| 4,774,937 | 10/1988 | Scholz et al. | 128/90 |
| 4,895,315 | 1/1990 | Salmela et al. | 242/66 |
| 5,266,115 | 11/1993 | Taccon et al. | 118/663 |

FOREIGN PATENT DOCUMENTS 0385082  9/1990  European Pat. Off. .

Primary Examiner—Katherine A. Bareford
Attorney, Agent, or Firm—Gary L. Griswold; Walter N. Kirn; James D. Christoff

[57] ABSTRACT

A web coating apparatus includes a supply roll of web and a wind-up spindle for receiving a discrete length of the web. Fluid is discharged from a coating die in a direction toward the wind-up spindle to coat the web as the web is wound about the wind-up spindle. A variable speed pump directs fluid through the coating die at flow rate that is proportional to the speed of advancement of the web. The apparatus is particularly useful for coating discrete lengths of orthopedic splinting and casting tape that is packaged for single patient use.

7 Claims, 9 Drawing Sheets

WEB COATING APPARATUS

This is a continuation of application Ser. No. 08/301,258 filed Sep. 6, 1994 now U.S. Pat. No. 5,501,738.

BACKGROUND OF THE INVENTION

1. Field of the Invention

This invention relates to an apparatus for applying a coating to a web. The invention is particularly useful for applying a precise quantity of a coating to a discrete length of web in automated fashion.

2. Description of the Related Art

Web coating apparatus is widely used in the manufacture of a variety of goods. For example, web coating apparatus is commonly used for making pressure sensitive adhesive tapes, wherein adhesive is applied to a web that serves as a substrate or backing of the tape. Other examples include apparatus for making photographic film, coated paper, magnetic audio, video and data storage tapes, as well as other products.

During the manufacture of coated webs, it is often desired to regulate the flow rate of liquid material applied to the web so that a coating having a generally uniform thickness is achieved. In the manufacture of many goods, coatings are applied by spraying the liquid through nozzles toward the web at a flow rate that is controlled by valves. Such practice is generally satisfactory for webs that are relatively long once the web reaches a constant speed during its travel next to the nozzles. In some instances, solenoid operated fluid control valves or variable flow rate pumps have been provided to automatically increase or decrease the fluid flow rate in proportion to the speed of movement of the web.

In certain other web coating processes, a web is directed over a drum and is overcoated, or flooded, with a quantity of fluid material. Before the web is released from the drum and advances toward a wind-up roll, a blade skives excess fluid from the web so that a smooth, substantially uniform coating is achieved.

Overcoating processes for coating webs are used for the manufacture of orthopedic splinting or casting tape, such as Scotchcast™ brand and Scotchcast Plus™ brand synthetic casting tape (from 3M). Scotchcast™ brand and Scotchcast Plus™ brand synthetic casting tape include a porous knit fiberglass backing that is coated with a water curable polyurethane resin.

Many processes that involve the coating of webs include a converting operation that occurs after the web has been coated and wound into an intermediate roll. The converting operation includes a rewinding step, where the intermediate roll is unwound and the coated web is wound to a final roll. The converting operation includes cutting steps, so that a relatively long coated web is cut into relatively small sections as may be appropriate for the end use.

In recent years, there has been increased interest in orthopedic splinting and casting tapes that are available in a variety of colors. The Scotchcast™ brand and Scotchcast Plus™ brand casting tape, for example, include a resin having appropriate dyes to provide a desired color. Some individuals ask for casting tape with bright colors, while others request casting tapes that are less conspicuous.

Unfortunately, polyurethane resin is tenacious and difficult to clean from the overcoating apparatus and the converting apparatus at the end of a coating operation, causing difficulties when attempts are made to manufacture casting tapes of different color. Moreover, the resin immediately begins to cure when exposed to ambient air because of moisture vapor that is present in the air. For these reasons, cleaning of the overcoating apparatus and the converting apparatus is typically a laborious, time consuming task that often entails the use of hazardous solvents.

Another concern during web coating operations is the amount of tension that is present in the finished, coated web. For example, orthopedic casting tape having a porous knit fiberglass backing is an advantage in that the backing can be stretched as needed when applied to the patient for conforming to the patient's anatomy. During manufacture of such casting tape, it is desirable to wind the tape into a final roll wherein the fiberglass backing as packaged is not stretched to any significant degree. The backing will then be able to be stretched as needed during application as the final roll is unwound in order to facilitate conforming the tape to the patient's anatomy.

The desirability of a coated web that is packaged in roll form in a substantially unstretched condition is not limited to coated webs used in the orthopedic field. For example, it may be desirable to provide a resin impregnated fabric in an unstretched condition for use in constructing or repairing automotive, marine or aerospace bodies so that the backing can be stretched as needed by the user and shaped to an appropriate configuration.

Many conventional web coating and converting operations are carried out by applying tension to the web to keep the web taut. Such processes may be suitable for coating nonelastic webs, but are generally unsatisfactory for coating elastic webs such as orthopedic tape backings. Further, if sufficient tension is applied to the web during the coating operation to stretch the web past its yield point, the web may no longer have physical characteristics that are suitable for its intended used.

SUMMARY OF THE INVENTION

The present invention in one embodiment is directed toward a web coating apparatus that includes a supply roll having a quantity of web, and a wind-up spindle for receiving a discrete length of the web from the supply roll. Means is provided for directing a leading edge portion of the web toward a wind-up spindle. The apparatus also includes a controller, and a variable speed drive mechanism connected to the controller for rotating the wind-up spindle to wind the web about the wind-up spindle. A source of fluid is provided, and a pump is connected to the source of fluid. Piping is in communication with the pump and the source of fluid, and the piping includes at least one outlet for directing the fluid onto the web. Means is connected to the controller for automatically increasing and decreasing the flow rate of fluid through the at least one outlet in proportion to the speed of movement of the web. A cutter is connected to the controller for cutting the web into the discrete length.

Another embodiment of the invention is directed to a web coating apparatus that comprises a supply roll having a quantity of web and a wind-up spindle for receiving at least a portion of the web from the supply roll. A drive mechanism is provided for advancing the web from the supply roll toward the wind-up spindle. A source of fluid is provided for coating the web, and a pump is connected to the source of fluid. Piping is in communication with the pump, and the piping includes an outlet that is located in a position to discharge fluid in a direction toward the wind-up spindle in order to coat the web as the web is received on the wind-up spindle.

The present invention in another embodiment is directed to a method of coating a web, and comprises the step of winding a length of web about a wind-up spindle. The method further includes the step of directing a fluid toward the wind-up spindle in order to coat the web as the web is wound about the wind-up spindle.

The present invention provides a significant advantage over conventional web coating apparatus and methods, in that the converting operation may be eliminated so that capital costs and costs associated with cleaning the apparatus are substantially reduced. The invention is particularly suitable for coating relatively short lengths of web that are individually packaged, and can be carried out in such a fashion that the web is not stretched to any significant degree during the coating operation or once packaged in roll form.

DETAILED DESCRIPTION OF THE PREFERRED EMBODIMENTS

Figure 1:
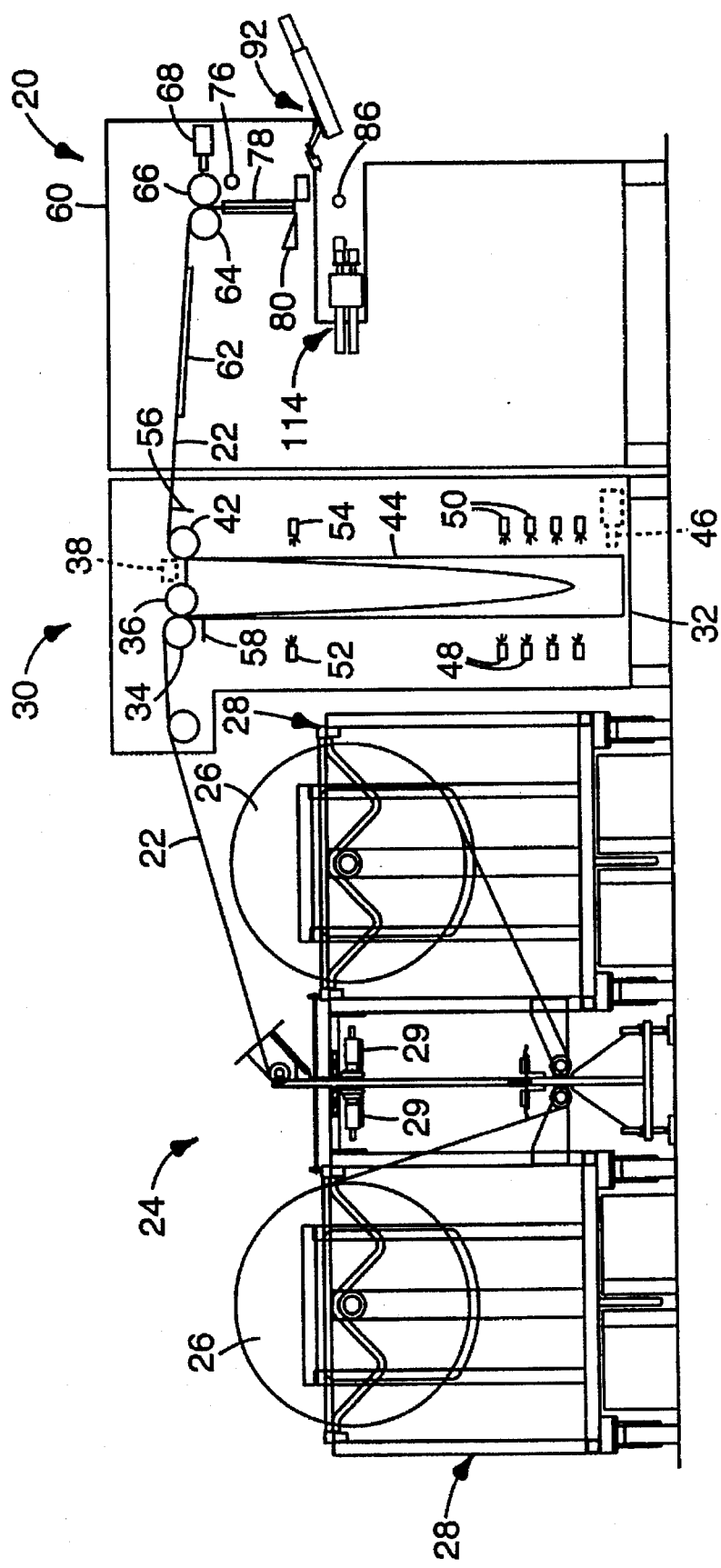
FIG. 1 is a side elevational view in partially schematic form of a web coating apparatus in accordance with the principles of the present invention, and wherein is also shown an automated web unwinding and splicing apparatus.

Referring initially to FIG. 1, an automated web coating apparatus is broadly designated by the numeral 20 and is adapted to apply a precisely measured quantity of a fluid or coating to an elongated web 22. The apparatus 20 receives the web 22 from an automated unwinding and splicing apparatus 24.

The unwinding and splicing apparatus 24 contains a number of initially separate rolls 26 (e.g., up to ten rolls) of the web material. Up to five rolls 26 are supported on each of two carts 28. As one roll 26 is depleted, a sensor detects the trailing edge of the web material and a pair of splicing members 29 are activated to push a leading edge of another roll 26 into contact with the trailing edge of the depleted roll 26. A section of pressure sensitive adhesive tape, having adhesive on both sides and previously affixed to a leading edge portion of the awaiting roll 26, bonds the leading edge portion of the awaiting roll 26 to the trailing edge portion of the depleted roll 26 for splicing the web material together. After each roll 26 is unwound, its supporting cart 28 advances in order to bring another roll 26 to a stand-by position for subsequent splicing and unwinding.

Further details of the unwinding and splicing apparatus 24 are described in a copending U.S. patent application entitled "Web Unwinding and Splicing Apparatus", U.S. Pat. No. 5,584,446 filed on even date herewith and assigned to the assignee of the present application, the content of which is hereby incorporated into the disclosure of the present specification. However, other unwinding apparatus is also possible. For example, a single roll of web material could also be satisfactorily employed so long as the roll was sufficiently large to provide a substantial length of web material before the roll is depleted. As such, frequent interruption of operation of the web coating apparatus 20 is avoided.

The web coating apparatus 20 includes a detensioning device 30 for decreasing tension on the web as it advances along its path of travel. The detensioning device 30 is located immediately downstream of the unwinding and splicing apparatus 24 and includes a drive roller 34 and a nip pressure roller 36. Both of the rollers 34, 36 are covered with a synthetic rubber material having a durometer hardness of about 60.

The drive roller 34 is mounted on a horizontal shaft that is connected to a DC variable speed motor 35 (model no. CDB 3538-11, from Baldor) shown schematically in FIG. 8. The motor 35 connected to a servodrive 37 (BR Brushless DC Drive, from Saftronics). The motor 35 is operable to rotate the roller 34 about a horizontal axis. A bearing block connects the shaft to a frame 32 of the detensioning device 30.

The roller 36 is mounted on a bracket that is connected to a piston rod of a double acting pneumatic piston and cylinder assembly 38 (model no. SE5-4.0, from Mills Specialty Products). The piston of the piston and cylinder assembly 38 is movable in a horizontal direction to move the roller 36 either toward or away from the roller 34.

Figure 8:
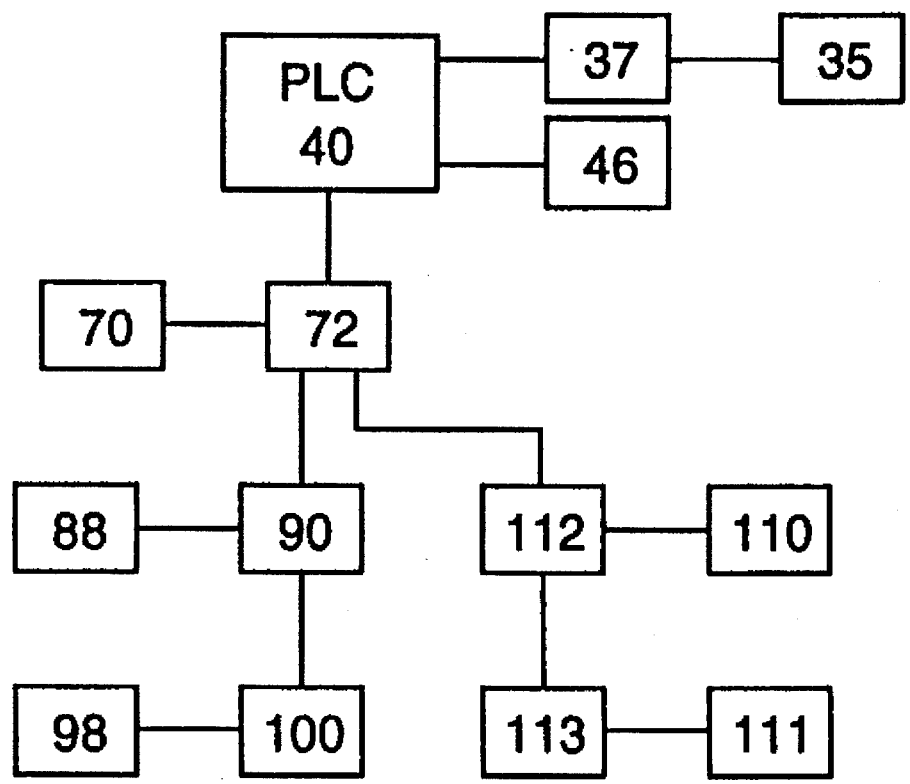
FIG. 8 is a schematic illustration showing the functional relationship of certain elements of the apparatus along with a controller for controlling the various elements.

A programmable logic controller 40 (series 90-30; G. E. Fanuc), shown schematically in FIG. 8, is electrically connected to solenoid operated air valves that are interposed in separate lengths of tubing that interconnect a source of pressurized air and each end of the cylinder of the piston and cylinder assembly 38. As such, the controller 40 is operable to open or close the nip between the rollers 34, 36. The controller 40 is also electrically coupled to the drive 37.

An idler roller 42 is mounted on a shaft fixed to the frame 32 in a position horizontally adjacent the roller 36. A detensioning chamber 44 having an open top is located below the rollers 36, 42. As the web 22 passes from the nip between the rollers 34, 36 and to the roller 42, a section of the web 22 freely hangs in the chamber 44 as illustrated in FIG. 1.

An air blower 46 (model no. R4310A-2; Gast Mfg. Corp.) is electrically coupled to the controller 40. The air blower 46 is connected by flexible tubing to a port near the lower end of the chamber 44. When the air blower 46 is activated by the controller 40, the air blower 46 draws air through the chamber 44 in a downwardly direction to facilitate the web 22 in hanging in an untangled, generally U-shaped configuration without appreciable tension.

Four photocells 48 are mounted on the frame 32 in a vertically spaced array near the lower end of one side of the chamber 44, and each photocell 48 is positioned to receive light from one of four light sources 50 located on the opposite side of the chamber 44. A fifth photocell 52 is mounted on the frame 32 near the upper end of the chamber 44, and is arranged to receive light from a light source 54 mounted on the opposite side of the chamber 44. The photocells 48, 52 and the light sources 50, 54 are all connected to the controller 40.

The lower photocells 48 provide an indication to the controller 40 of the extent of web 22 hanging in the chamber 44. When, for example, the upper photocell of the four photocells 48 senses light from the upper light source 50, the controller 40 increases the speed of the motor 35 connected to the roller 34 in order to increase the extent of web 22 hanging in the chamber 44. On the other hand, if the lower photocell of the four photocells 48 fails to detect light from the lower light source of the light sources 50, the speed of the motor 35 is decreased in order to decrease the length of web 22 hanging in the chamber 44.

The fifth photocell 52 provides an emergency function. If, for example, the photocell 52 detects light from the light source 54, the extent of web 22 hanging in the chamber 44 is nearly exhausted as might occur, for example, when the supply of web from the unwinding and splicing apparatus 24 is depleted, or when the web 22 is jammed in the apparatus 24 and unable to further advance. In such an instance, the controller 40 will immediately interrupt further operation of the apparatus 20 and provide a signal to the operator that attention is needed.

A brush 56 is fixed to the frame 32 and is mounted immediately downstream of the idler roller 42 for contact with the web 22 as the web 22 advances. Another brush 58, similar to brush 56, is fixed to the frame 32 immediately downstream of the nip between the rollers 34, 36 for engagement with the advancing web 22. The brushes 56, 58 are made of carbon fiber or stainless steel and reduce the amount of static electricity in the web 22.

The web coating apparatus 20 includes a second frame 60 that is secured to and optionally integral with the frame 32. An inclined guide 62 is mounted on brackets fixed to the frame 60. The guide 62 has a channel that receives and guides movement of the web 22 as the latter advances from the idler roller 42 and toward a nip between a metering roller 64 and a nip pressure roller 66.

The nip pressure roller 66 rotates on bearings about a shaft that is fixed to a bracket. The bracket is connected to a piston rod of a double-acting piston and cylinder assembly 68 (model SE5-4.0, from Mills Specialty Products). Each end of the cylinder of the piston and cylinder assembly 68 is connected by tubing to the source of pressurized air mentioned earlier. The piston and cylinder assembly 68 is coupled by brackets to the frame 60.

A pair of solenoid operated air valves are interposed in the tubing interconnecting the pressurized air source and the piston and cylinder assembly 68, and the air valves are electrically connected to the controller 40. As such, the controller 40 can open or close the nip between the rollers 64, 66 when desired. Both of the rollers 64, 66 are covered with a synthetic rubber material that has a durometer hardness of 60 and that is similar to the synthetic rubber material on the rollers 34, 36.

The metering roller 64 is connected to a shaft supported by bearings that are connected to the frame 60. The roller 64 and the shaft are coupled to a servomotor 70 (model DXM-340W; Emerson Electronic Motor Controls) for rotation about a horizontal axis. The servomotor 70 is schematically, illustrated in FIG. 8, and is electronically connected to a servodrive 72 (Model No. DXA-340, PCM-5 ratio controller, from Emerson Electronic Motor Controls) that is electrically connected to the controller 40. The servomotor 70 includes a built-in resolver connected to the servodrive 72 for confirming the rotative position of the servomotor 70 and hence of the metering roller 64 at all times that the apparatus 20 is in operation.

A brush 74, similar to brushes 56, 58 is optionally mounted immediately below the metering roller 64 for contact with the passing web 22 to reduce any static electricity charge in the web 22. As another option, an electric, ionized gas static electricity reducing element 76 (such as the Shockless Static Bar, Model No. D1G7RY, from Simco Co.) is mounted on the frame 60 below the nip pressure roller 66 or optionally below the metering roller 64 in the space occupied by brush 74 in FIGS. 2–7. Alternatively, a nuclear ionizer or high voltage ionizer could be used to reduce static electricity charge in the web 22.

As illustrated in FIG. 1 as well as in FIGS. 2–7, a stationary guide member 78 is fixed to the frame 60 below the nip between the rollers 64, 66, and includes a vertical channel for guiding movement of the web 22 as it descends. From the guide member 78, the web 22 passes through an opening of a cutter (model SC-6; Azco Corp.). The cutter includes a guillotine-type cutting knife 80 as well as an anvil 82.

The knife 80 is connected to a piston rod of a double-acting pneumatic piston and cylinder assembly 84. A pair of solenoid operated air valves are connected to tubing that interconnects the pressurized air source and each end of the cylinder of the piston and cylinder assembly 84, and the air valves are electrically coupled to the controller 40.

A wind-up spindle 86 includes a shaft that is connected to a servomotor 88 (model no. DXE-316W; Emerson Electronic Motor Controls). The shaft rotates about a horizontal axis that is below and laterally offset from a vertical reference axis that passes through the channel of the guide member 78 and the channel of the cutter. The servomotor 88 is electrically coupled to a servodrive 90 (Model No. DXA-340, PCM-5 ratio controller, from Emerson Electronic Motor Controls) and includes a resolver for confirming the rotative position of the wind-up. spindle 86 at all times. As illustrated in FIG. 8, the servodrive 90 is electrically connected and is a slave to the servodrive 72.

A coating die assembly 92, shown in more detail in FIGS. 2–7, is mounted to one side of and slightly above the wind-up spindle 86. The coating die assembly 92 includes screwdrive mechanism 94 (LM guide actuator from THK) having a subframe secured by brackets to the frame 60. The mechanism 94 includes a sliding carriage 96 that is movable along an upper channel of the subframe in an upwardly or downwardly inclined direction.

A drive screw of the screwdrive mechanism 94 is rotatably driven by a servomotor 98 (model DXM-205; Emerson Electronic Motor Controls) that is mounted on the subframe. The servomotor 98 is electrically connected to a servodrive 100 (Model No. DXA-340, PCM-5 ratio controller, from Emerson Electronic Motor Controls) that is in turn electrically connected to and is a slave to the servodrive 90 as schematically shown in FIG. 8.

A coating die 102 is detachably mounted on a bracket that is located on the upper end of the sliding carriage 96. The coating die includes an inlet passageway, an outlet passageway and an inner cylindrical chamber that serves as a manifold to distribute incoming fluid from the inlet passageway to all regions of the outlet passageway. The outlet passageway has a width that is approximately equal to the width of the web 22, and preferably includes a series of spaced apart nozzles such that an aligned array of distinct, spaced apart outlets are provided. Each nozzle is made of a rigid metal tube having a flattened outer end.

An insert is slidably, removably received in the chamber of the coating die 102, and includes a body portion with a shape that is adapted to distribute fluid at equal flow rates through each of the nozzles across the width of the coating die 102. To this end, the body portion of the insert is machined on a lathe to a configuration such as a dogbone shape or a convex shape as may be needed to provide equal flow rates of fluid through each outlet of the outlet passageway.

Preferably, the coating die 102 also includes a channel that extends through the die housing parallel to the chamber. The channel is coupled to a source of hot water or other fluid controlled by the controller 40, in order to elevate the temperature of the die housing above ambient for enhancing the flow of fluid moving through the chamber. A thermocouple is also connected to the die housing and electrically coupled to the controller 40 for monitoring temperature of the housing.

Further details and alternative constructions of the coating die 102 are set out in a copending U.S. patent application entitled "Die for Extruding a Fluid Stream" U.S. Pat. No 5,516,273 filed on even date herewith and assigned to the assignee of the present application, the content of which is expressly incorporated by reference herein. Other means for applying the fluid to the web 22 are also possible. For example, the coating die 102 may be replaced by a spray head that atomizes the fluid.

The coating die 102 is part of piping 104 for directing fluid from a fluid source 106 onto the web 22. The fluid source 106 comprises a 5 gallon (19 liter) storage cylinder having a cover, and a dry gas such as nitrogen purges the cylinder to hinder curing of the fluid (that, as described below, may be a water curable synthetic resinous material).

An electric heater is also connected to the storage cylinder of the fluid source 106 to maintain the fluid in the cylinder at a temperature of approximately 50° C. The heater for the fluid source 106, as well as a thermocouple to monitor the temperature of the fluid source 106, are electrically coupled to the controller 40.

The piping 104 includes a section of tubing that interconnects the fluid source 106 and a pump 108, as well as a second section of tubing that interconnects the pump 108 and the coating die 102. The pump 108 is a gear pump (100 cc/rev, 20/1 gear reduction, BPB series; from Zenith) that is rotatably driven by a servomotor 110 (model no. DXM-6120; Emerson Electronic Motor Controls).

The servomotor 110 is electrically connected to a servodrive 112 (Model No. DXA-340, PCM-5 ratio controller, from Emerson Electronic Motor Controls) that is schematically depicted in FIG. 8. The servodrive 112 is electrically connected and is a slave to the servodrive 72. Thus, the servodrive 112 represents a means to automatically increase or decrease the flow rate of fluid through the die outlet in proportion to the rotational speed of the metering roller 66, to the rotational speed of the wind-up spindle 86, and hence also to the speed of movement of the web 22. The servomotor 110 includes a resolver to confirm its rotative position.

Preferably, a dye injection system is provided to inject a colorant into the piping 104, and specifically into the second section of tubing that interconnects the pump 108 and the coating die 102. The dye injection system includes a container (not shown) for holding a quantity of dye and a gear pump (1.168 cc/rev 3/1 gear reduction, BPB series; from Zenith) connected by a third section of tubing to the container. A fourth section of tubing is coupled to the pump and the second section of tubing. A static mixer is located in the second section of tubing downstream from its junction with the fourth section of tubing and thoroughly mixes the colorant with the resin or other fluid from the fluid source 106.

The dye injection pump is driven by a servomotor 111 (VN-MD: S3016, from Emerson Electronic Motor Controls) that is schematically depicted in FIG. 8. The servomotor is coupled by a right angle drive (Model No. MH015A129-2, from Textron) to the pump. The servomotor is electrically connected to a servodrive 113 (Model No. DXA-318, PCM-2S electronic sync ratio controller, from Emerson Electronic Motor Controls) that is, in turn, electrically connected and a slave to the servodrive 112.

An air bump slide assembly 114 includes a support 116 that is fixed to the frame 60. A first slide 118 of the assembly 114 is slidably coupled to the support 116 and is guided for movement by a piston rod of a double-acting pneumatic piston and cylinder assembly 120 (Model No. SE2-4.0, from Mills Specialty Products). The piston and cylinder assembly 120 is connected by tubing to the previously mentioned pressurized air source. Solenoid operated air valves coupled to the tubing are electrically coupled to the controller 40 for horizontal movement of the first slide 118 relative to the housing 116 when desired.

The air bump slide assembly 114 also includes a second slide 122 that is slidably coupled to the support 116. The second slide 122 is connected to a piston rod of a double-acting pneumatic piston and cylinder assembly 124 (Model No. SE2-4.0, from Mills Specialty Products) that is connected by tubing to the source of pressurized air. Solenoid operated air valves coupled to the tubing are electrically connected to the controller 40 in order to horizontally move the second slide 122 relative to the support 116 when desired.

A bar 125 is fixed to the first slide 118, and extends upwardly for releasable contact with the second slide 122. As the first slide 118 is moved by the piston and cylinder assembly 120 toward a fully extended position (i.e., toward the right-hand side of FIGS. 1–7), the bar 125 engages the second slide 122 and moves the latter in synchronization with movement of the first slide 118. When the second slide 122 is moved toward a fully extended position by the piston and cylinder assembly 124 in instances when the first slide 118 is fully extended, the second slide 122 disengages the bar 125 and moves past its previous position that was directly adjacent the first slide 118.

An air nozzle 126 having a series of spaced-apart air outlets is secured to a forward end of the second slide 122. The air nozzle 126 is coupled by tubing to the source of pressurized air, and a solenoid operated air valve connected to the controller 40 enables the air nozzle 126 to emit a blast of pressurized air when desired.

Figure 2:
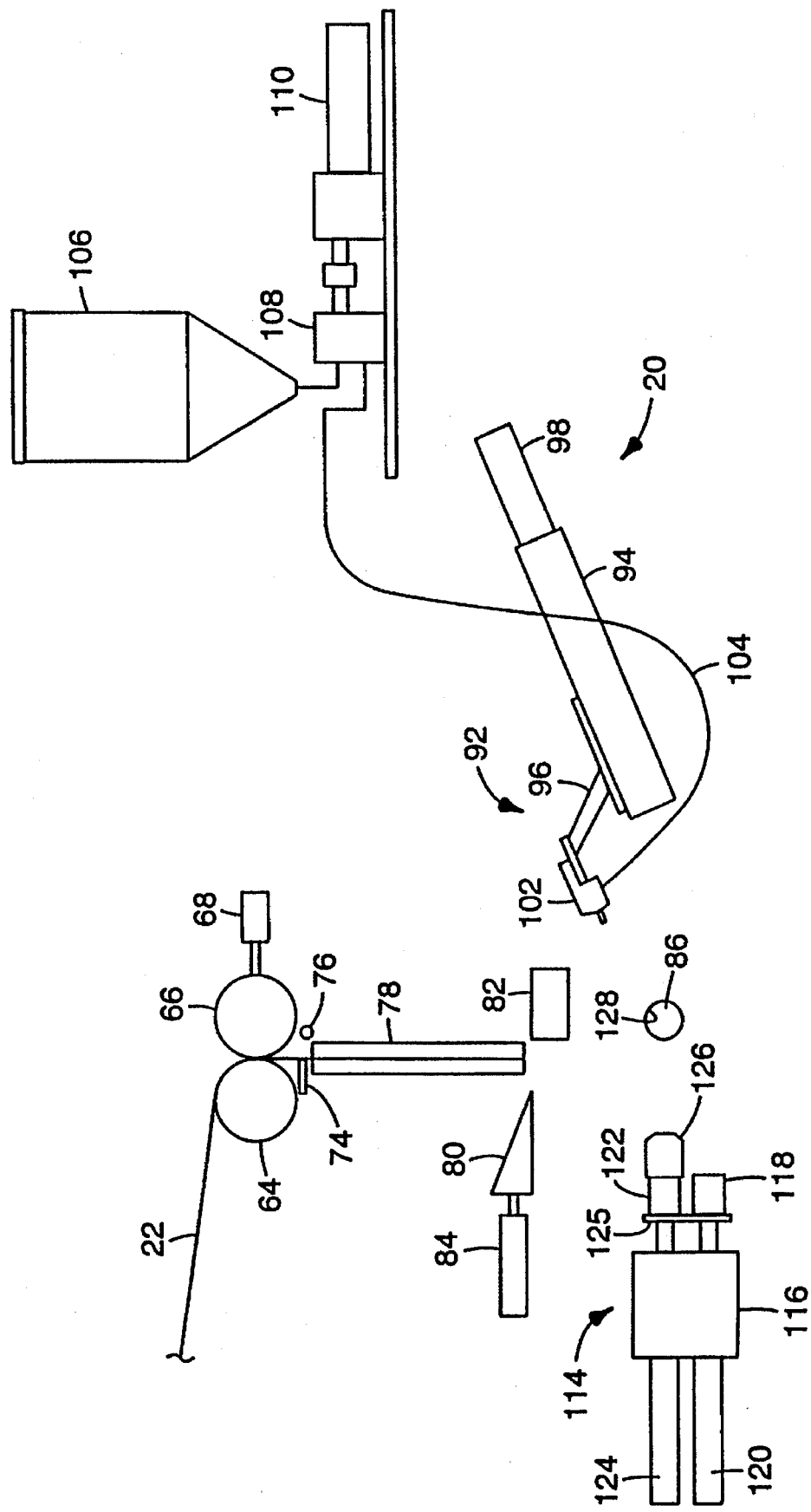
FIG. 2 is an enlarged side elevational view in partially schematic form of a portion of the web coating apparatus illustrated in FIG. 1.
Figure 3:
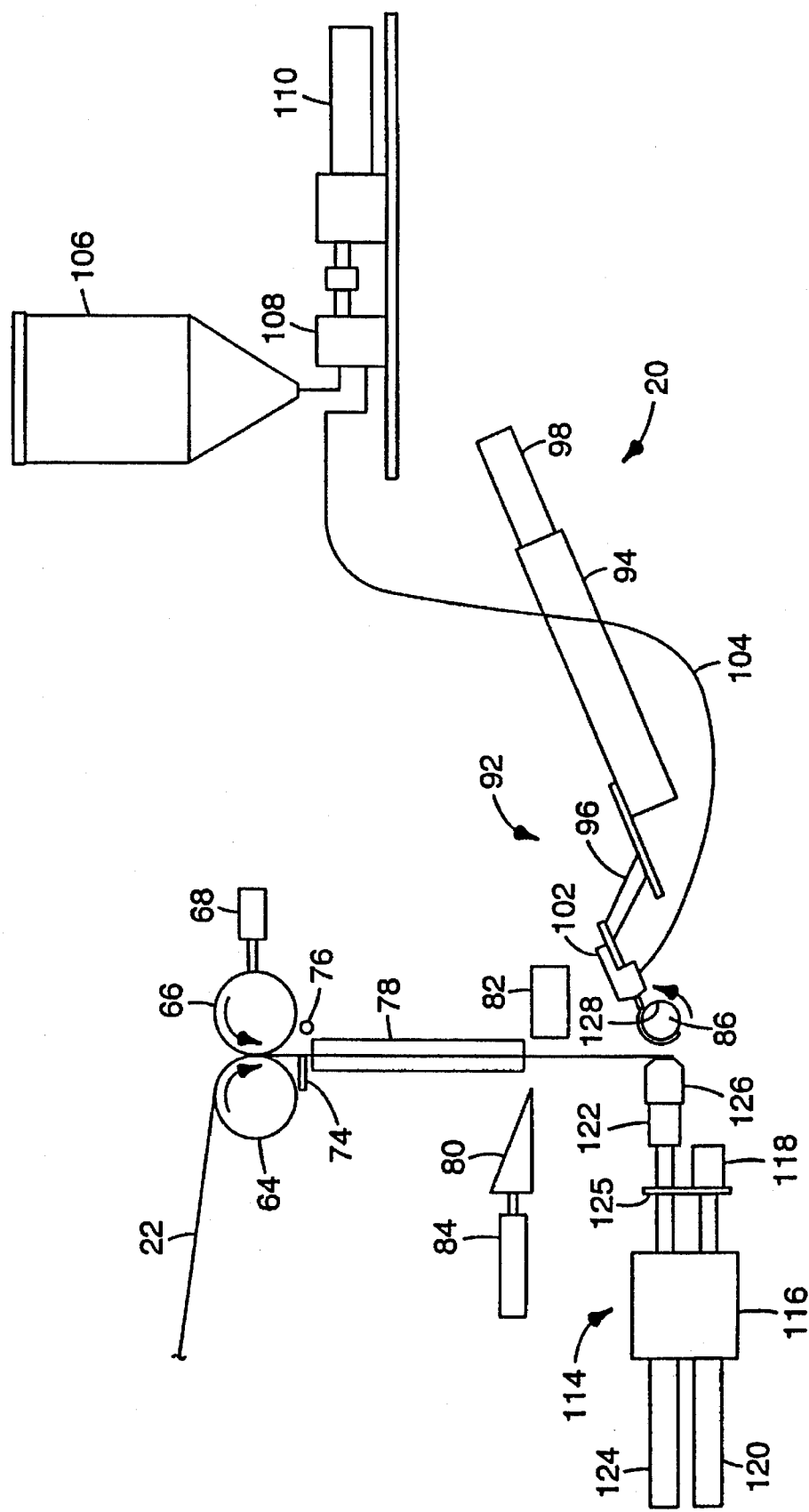
FIG. 3 is a view somewhat similar to FIG. 2 except that a web has descended from its orientation shown in FIG. 2, an air bump assembly has advanced toward a leading edge of the web, and a coating die has been advanced toward a rotating wind-up spindle in order to apply fluid to a core received on the wind-up spindle.
Figure 4:
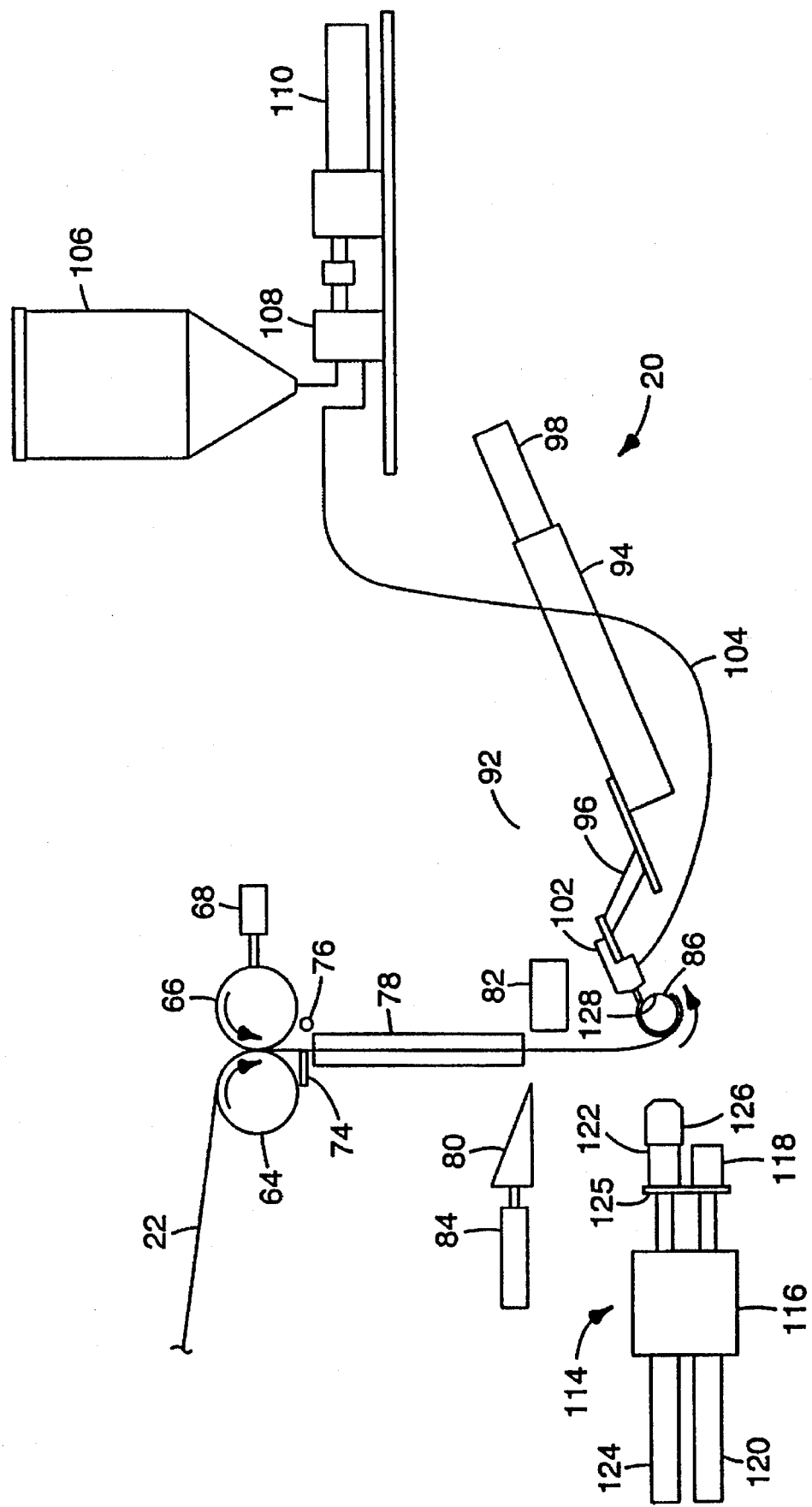
FIG. 4 is a view somewhat similar to FIG. 3 except that the leading edge of the web is partially wound about the wind-up spindle, the air bump assembly is retracted to an intermediate position and additional fluid has been applied to the core.
Figure 5:
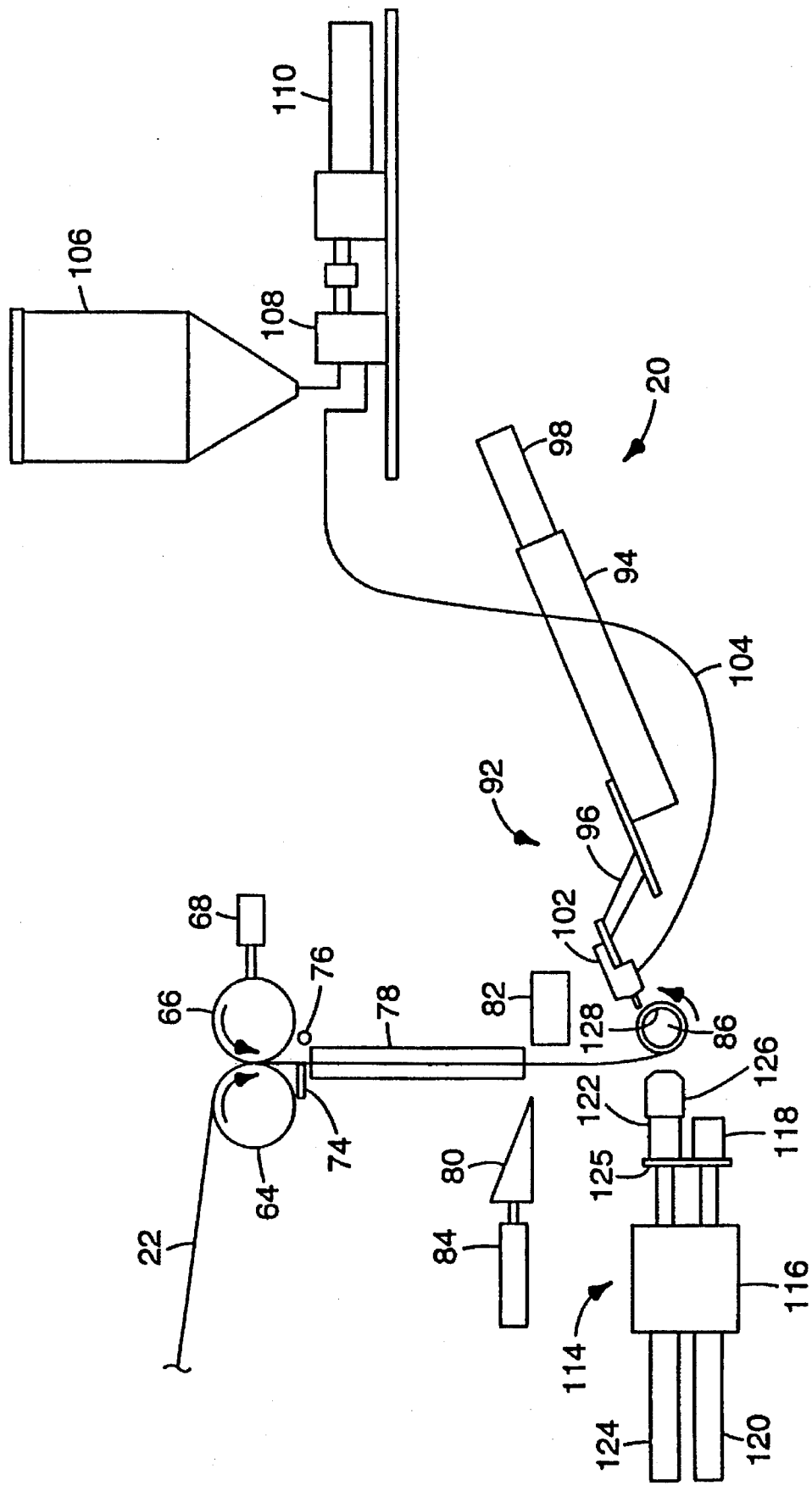
FIG. 5 is a view somewhat similar to FIG. 4 except that the coating die has been moved slightly away from spindle as additional web is wound about the core.
Figure 6:
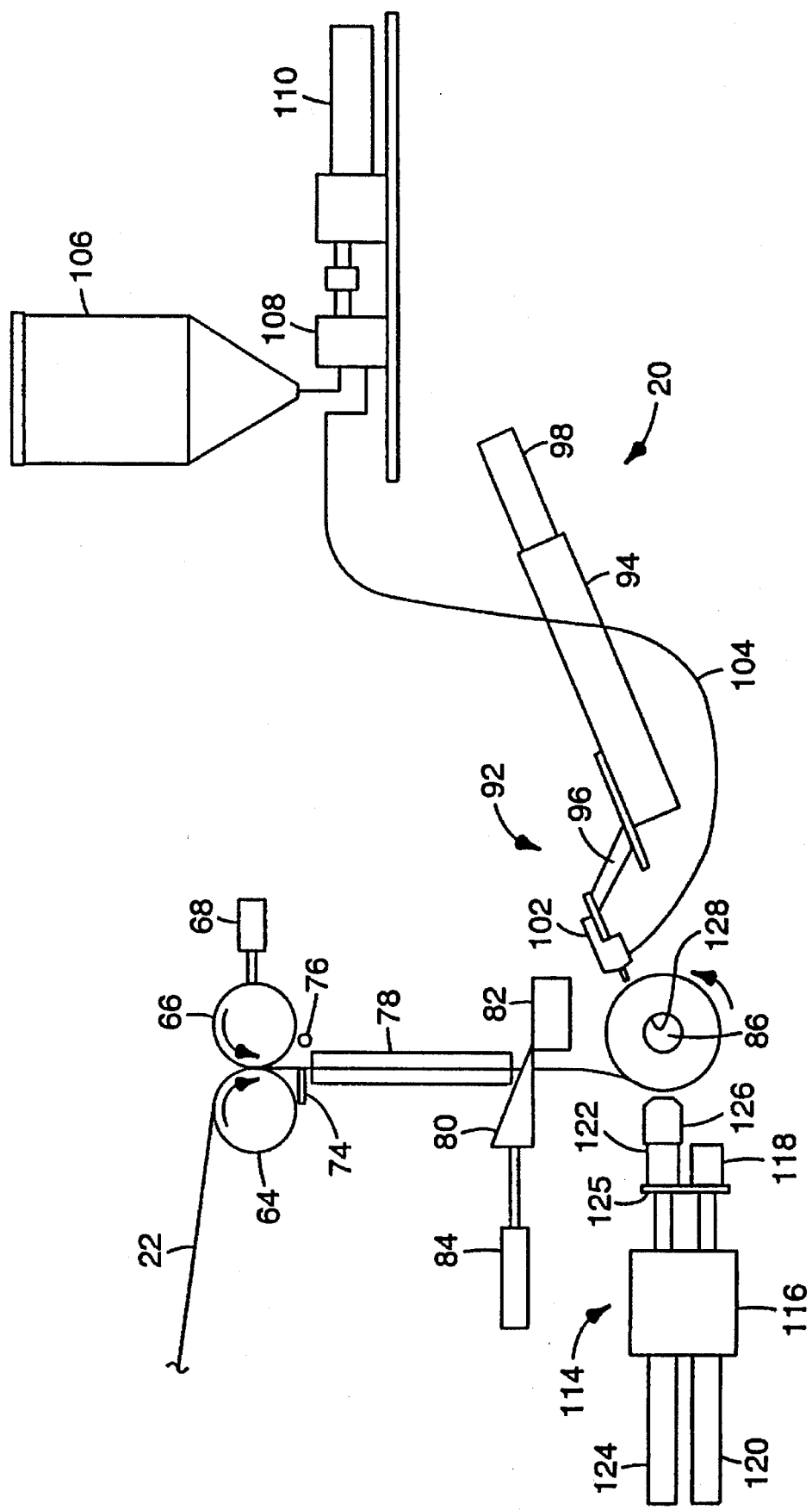
FIG. 6 is a view somewhat similar to FIG. 5, but wherein the coating die is illustrated as moved further away from the spindle, wherein additional web has been wound about the core, wherein a cutter has been advanced to cut the web and wherein the air bump assembly has been advanced in readiness to urge the trailing edge of the web toward the wind-up spindle.
Figure 7:
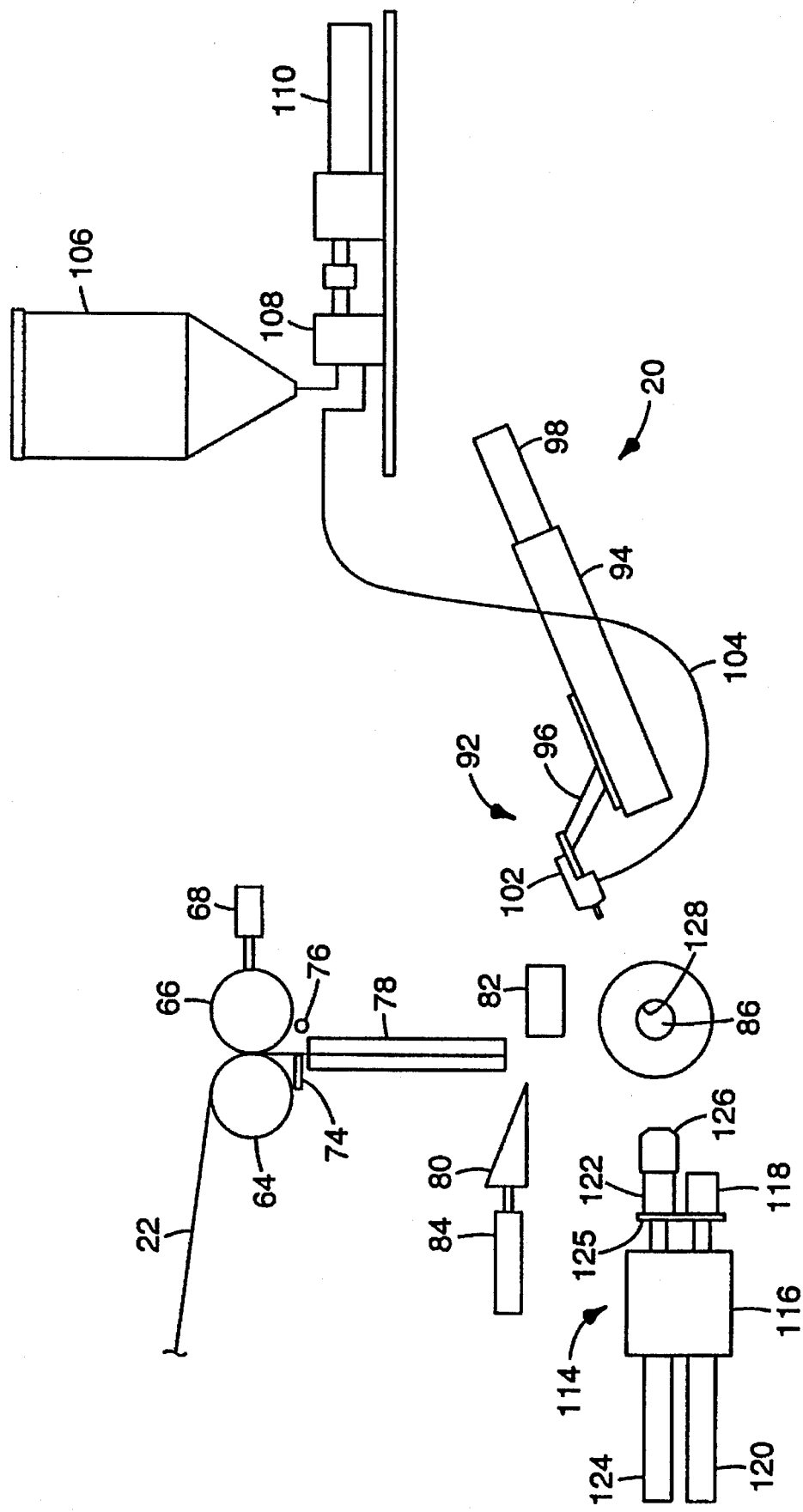
FIG. 7 is a view somewhat similar to FIG. 6 except that the trailing edge of the web has been wound about the spindle, the coating die has moved further away from the wind-up spindle, the air bump assembly has retracted to its intermediate position and the cutter has retracted to enable subsequent passage of the web.

The air bump slide assembly 114 is shown in its fully retracted position in FIGS. 2 and 7. In FIG. 3, both the first slide 118 and the second slide 122 are shown in their extended orientation. In FIGS. 4-6, the first slide 118 is in its extended position, while the second slide 122 is in its retracted position. The assembly 114 serves as a means to push the leading and trailing edge of the discrete length of web 22 toward and into contact with the wind-up spindle 86.

Figure 9:
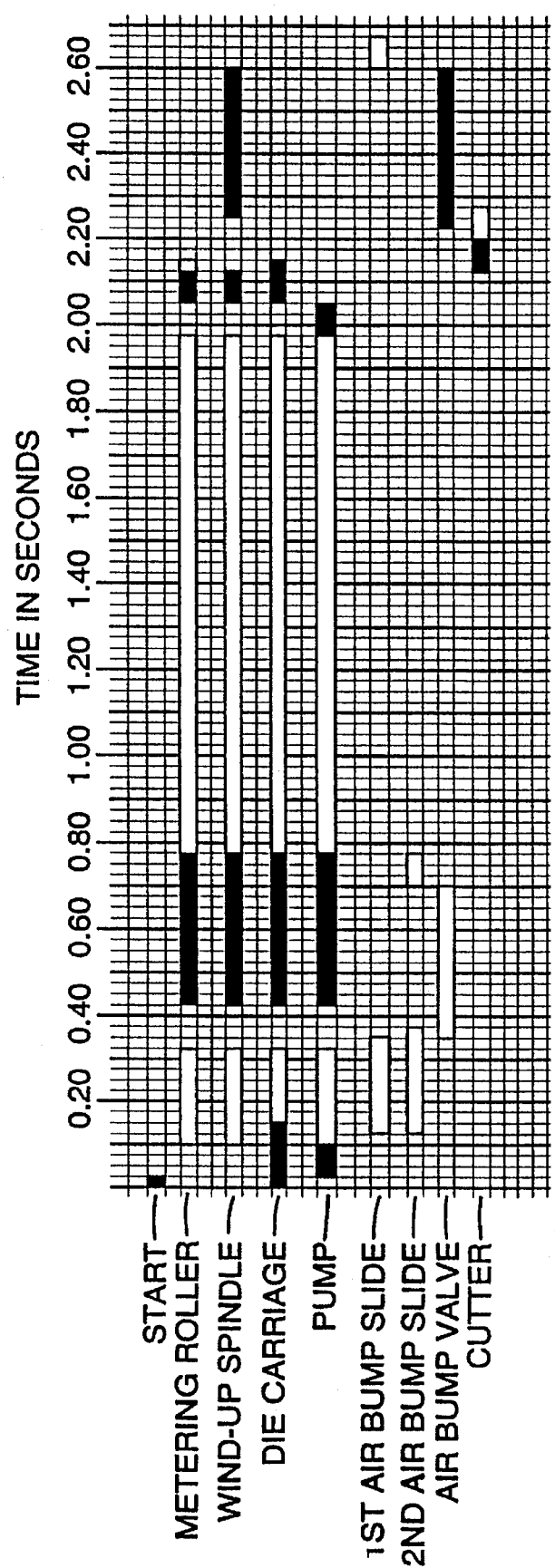
FIG. 9 is an exemplary timing chart which illustrates the sequence of operation of various elements.

The operation of coating the web 22 with fluid shall now be described. FIG. 9 is an exemplary timing chart of the web coating apparatus 20 that illustrates the sequence of movement of various elements over a relatively short period of time (e.g., 2.68 seconds) to coat a discrete length of the web 22.

FIG. 2 illustrates the apparatus 20 as it schematically appears at time 0.00 on the timing chart, at the beginning of a coating operation. The drive roller 34 is controlled for rotational movement by the controller 40 independently of movement of the servomotors 70, 88, 98 or 110. In FIG. 2, the leading edge of the web 22 is located just above the knife 80, and a polypropylene core 128 has been placed on the wind-up spindle 86. The core 128 includes a protruding, longitudinally extending tab that is received in a mating slot of the wind-up spindle 86.

As shown in FIG. 9, the servomotor 98 for the coating die assembly 92 is activated upon initiation of a coating cycle. The servomotor 98 is rotated to move the carriage 96 and the die 102 toward the core 128. Immediately thereafter, the servomotor 110 is energized to rotate the pump 108 slowly, or in "drip" mode, to insure that fluid in the coating die 102 is thereafter present at the die outlet in readiness for application.

At 0.10 seconds, the servomotors 70, 88 are energized to rotate the metering roller 64 and wind-up spindle 86 respectively. At the same time, the speed of the servomotor 110 is increased so that the pump 108 increases the flow rate of fluid in the piping 104. As a consequence, fluid is immediately discharged from the coating die 102 onto the core 128 as the latter rotates. The servomotor 98 continues to rotate for an additional 0.05 seconds to bring the coating die 102 somewhat closer to the core 128. At 0.15 seconds, however, the servomotor 98 reverses direction to cause the carriage 96 and coating die 102 to begin ascending in a direction away from the wind-up spindle 86. Both slides 118, 122 also begin to extend at this time.

FIG. 3 illustrates the apparatus 20 at 0.325 seconds into the coating cycle. At this time, the leading edge of the web 22 has descended to a position horizontally adjacent the air nozzle 126, and slightly less than one-half of the periphery of the core. 128 has been coated with fluid. At 0.325 seconds, rotation of the servomotors 70, 88, 98 and 110 is interrupted, although the piston and cylinder assemblies 120, 124 continue to move the slides 118, 122 toward their respective fully extended orientations. At 0.35 seconds, pressurized air is supplied to the air nozzle 126 in order to push the leading edge of the web 22 into contact with the fluid present on the core 128. The fluid is tenacious and readily connects the leading edge to the core 128.

At 0.425 seconds, the servomotors 70, 88, 98 and 110 are energized to begin winding the web 22 onto the core 128. As the web 22 is wound on the core 128, the coating die assembly 92 continues to coat remaining portions of the core 128, and then apply a coating of fluid to the web 22 as it passes during winding on the core 128. At 0.70 seconds, air to the air nozzle 126 is interrupted, and the piston and cylinder assembly 124 is actuated to retract the second slide 122 to the position shown in FIG. 4.

FIG. 5 is a schematic illustration of the apparatus 20 after 0.775 seconds of operation of a cycle. At this time, approximately two wraps of the web 22 have been received on the core 128. Next, all of the servomotors 70, 88, 98 and 110 are increased in speed, and continue to run at the increased speed until 1.975 seconds.

As can be appreciated by comparing FIGS. 4, 5 and 6, movement of the carriage 96 supporting the coating die 102 is synchronized with winding of the web 22 on the core 128. As a consequence, the outlet of the coating die 102 is spaced at approximately the same distance from the web 22 (or the core 128 at the beginning of the operation) to facilitate application of a coating having a uniform thickness. As the diameter of the coated web roll on the spindle 86 increases, the servomotors 88, 98 decrease in speed relative to the speed of the servomotor 70 to match the linear speed of the web 22 as it advances toward the spindle 86.

At 1.975 seconds, rotation of the servomotor 110 is reversed to enable the pump 108 to withdraw or "suck back" a small amount of fluid into the coating die 102. Such a step facilitates control of the fluid stream, so that dripping or oozing is avoided.

Next, at 2.05 seconds the servomotors 70, 88 and 98 are again energized in order to wrap an additional short length of web 22 onto the underlying roll that has been previously coated with fluid. At 2.125 seconds, the metering roller servomotor 70 is rotated slightly to eliminate any tension in downstream portions of the web 22, and the piston and cylinder assembly 84 is actuated to move the knife 80 toward the anvil 82 and cut the web 22 as depicted in FIG. 6.

Pressurized air is directed through the air nozzle 126 at 2.225 seconds, and at 2.25 seconds the servomotor 88 is again energized to enable the trailing end portion of the cut length of web to wrap onto the roll on the wind-up spindle 86. Both the pressurized air to the air nozzle 126 and energization of the servomotor 88 continue until 2.60 seconds. Advantageously, as can be appreciated by reference to FIG. 6, the cut but unwound portion of the web 22 (i.e., the free, trailing end portion of the web 22 after cutting) has a length that is approximately equal to the length of coating applied to the wound web in a circumferential direction, so that little, if any, excess coating is present on the exterior of the finished wound web.

At 2.60 seconds, air pressure to the nozzle 126 is interrupted and the servomotor 88 is de-energized to stop rotation of the wind-up spindle 86. At 2.60 seconds, air pressure is directed to the cylinder of the piston and cylinder assembly 120 in order to retract the first slide 118 such that the air bump slide assembly 114 is returned to its fully retracted orientation. FIG. 7 is an illustration of the apparatus 20 at 2.675 seconds.

The wound, discrete length of coated web 22 and the core 128 are then immediately removed from the spindle 86 and packaged to avoid any adverse affects that may occur upon exposure of the fluid to the atmosphere. A particularly preferred packaging machine is described in pending U.S. patent application entitled "Spreader Bars for Packaging Machines and Associated Mechanisms", Ser. No 08/104,886, filed Aug. 10, 1993 and assigned to the assignee of the present application, the content of which is expressly incorporated by reference herein. Optionally, a removal mechanism comprising a plate slidable along the spindle 86 may be provided. The plate is connected to a piston rod of a double-acting pneumatic piston and cylinder assembly that is coupled by solenoid operated air valves to a source of pressurized air. The air valves are electrically coupled to the controller 40 for movement of the plate to horizontally eject the coated web and core from the spindle 86 once the air bump slide assembly 114 has retracted.

As another option, the wind-up spindle 86 is not directly connected to the frame 60, but instead is one of multiple (e.g., such as 8) wind-up spindles that are mounted on a horizontal turntable. The turntable is rotatable about a vertical axis by a servomotor that is connected to a servodrive coupled to the controller 40. The turntable is incrementally rotated about a partial arc to sequentially bring each wind-up spindle to the position of the wind-up spindle shown in FIGS. 1–7. Preferably, a core feeding apparatus places a core such as core 128 on each spindle before the spindles reach the position of the spindle 86 shown in FIGS. 1–7. In addition, an automated removal mechanism is provided for removing the wound, discrete length of coated web 22 from each spindle after the spindle has moved away from the position depicted in FIGS. 1–7. The removal mechanism includes a pair of fingers that are movable to pull the coated web and the core from each arriving spindle onto a concave, half-cylindrical recess of a transport guide. The guide is then pivoted upwardly about a horizontal axis to meet a stationary, upstanding, half-cylindrical guide. Next, a push rod urges the coated web and core to descend through the adjacent half-cylindrical guides and into a packaging machine such as the one described in the aforementioned U.S. patent application Ser. No. 08/104,886.

Preferably, the controller 40 is the same controller, or is electrically linked to a controller, that is controlling the operation of the unwinding and splicing apparatus 24. The controller 40 determines the location of any arriving splices that may be present in the advancing web 22. Once the spliced portion of the web 22 has been wound onto a core 128 received on the turntable, and the turntable has advanced, a second pair of fingers located upstream of the half-cylindrical transport guide pulls the spliced web and core into a reject bin for disposal.

The apparatus 20 is particularly useful for the manufacture Of orthopedic splinting or casting tape, such as Scotchcast™ brand or Scotchcast Plus™ brand casting tape in single-patient lengths. Such tape is coated with a water curable polyurethane resin as is described in U.S. Pat. Nos. 4,570,622, 4,502,479, 4,667,661 and 4,774,937. A suitable web is an annealed porous knit fiberglass material such as described in U.S. Pat. No. 4,609,578.

The water curable polyurethane resins used in orthopedic splinting and casting tape begin to cure when exposed to water vapor in the atmosphere. For this reason, the apparatus 20 is particularly useful in the manufacture of discrete lengths of the tape that are of a size (such as 12 ft., or 3.6 m) that is adapted for use by a single patient.

If desired, the apparatus 20 may be used in a dehumidified room to reduce the likelihood of undue curing of the resin. Alternatively, a cover or screen may be placed over the frame 60 and purged with a dry gas such as dehumidified air or nitrogen. Preferably, the rolled, coated discrete length of web 22 is packaged immediately after coating and before the resin has had an opportunity to absorb any significant amount of moisture.

Preferably, the apparatus 20 is adapted to enable coating of webs having different widths. For example, typical widths for orthopedic casting tape may range from approximately 1.0 inch (2.5 cm) to approximately 5.0 inch (12.5 cm). The various rollers such as rollers 34, 36, 42, 64, 66 and guides 62 are wider than the widest expected web, and the sides of the chamber 44 are adjustable so that webs of a various width can be accommodated.

As can now be appreciated, the metering roller 64, the wind-up spindle 86 and the servomotors 70, 88 serve as a means for advancing the web 22 from the supply roll 26 to the wind-up spindle 86, and for winding the web 22 about the wind-up spindle 86. Other drive mechanisms are also possible. For example, the metering roller 64 and the wind-up spindle 86 may be driven by other types of motors or web advancement devices. Some of the motors (i.e., servomotors 88 and 98) may be replaced by a single, common motor using appropriate motion transfer means such as a toothed belt or chain drive.

It can also now be appreciated that the servodrive 112 comprises a means for increasing and decreasing the flow rate of fluid through the outlets of the coating die 102 in timed, synchronous coordination with movement of the web 22 and in proportion to the speed of movement or winding of the web 22 as it advances along its path of travel toward the wind-up spindle 86. Other means are also possible. For example, the pump 108 may be mechanically linked to the metering roll 64, so that both the metering roller 64 and the pump 108 rotate simultaneously and fluid is discharged through the outlets of the coating die 102 in coordination with movement of the web 22. As another option, detectors operable to determine movement or speed of travel of the web 22 may be electrically coupled to a controller that energizes the pump servomotor 110 accordingly.

It can also be appreciated that the present invention is an advantage, in that little cleaning of the apparatus 20 is necessary in order to change the fluid, as might occur, for example, when resins of a different color are utilized. More specifically, inasmuch as the coating die 102 directs fluid only to the web 22 and the core 128, little, if any, cleanup of other adjacent areas of the apparatus 20 is needed other than to clean the coating die assembly 92, piping 104 and pump 108.

Other changes or additions to the embodiments described in detail above may also be apparent to those skilled in the art. Thus, the scope of the present invention should not be limited to the presently preferred embodiments described above, but only by the following claims and their equivalents.

What is claimed is:

1. A method of coating a web comprising the steps of:
   winding a length of the web about a wind-up spindle; and
   directing a fluid from at least one outlet of a coating die directly onto a portion of the web that has been received on the wind-up spindle in order to coat the web as the web is wound about the wind-up spindle, wherein said step of directing a fluid includes the step of moving the at least one outlet away from the wind-up spindle as the web is wound about the wind-up spindle in synchronous fashion such that the at least one outlet remains spaced at approximately the same distance from the web.

2. The method of claim 1, including the steps of placing a core over the wind-up spindle, and applying a quantity of said fluid on the core in order to connect a leading edge of the web to the core.

3. The method of claim 1, wherein said step of directing a fluid is carried out at a certain flow rate, and wherein said step of winding a length of the web is carried out at a certain speed, and including the step of varying the flow rate of fluid as the web is wound in accordance with the speed of winding the length of web about the wind-up spindle.

4. A method of coating a web comprising the steps of:
   winding a length of the web about a wind-up spindle; and directing a fluid toward the wind-up spindle in order to coat the web as the web is wound about the wind-up spindle, wherein said method includes the initial steps of advancing a leading edge portion of the web toward the wind-up spindle, and directing a pressurized stream of gas toward the leading edge portion of the web to urge the leading edge portion toward the wind-up spindle.

5. The method of claim 4, wherein said step of directing a fluid toward the wind-up spindle includes the steps of passing the fluid through at least one outlet, and moving the outlet away from the wind-up spindle as the web is wound about the wind-up spindle.

6. The method of claim 4, including the steps of placing a core over the wind-up spindle, and applying a quantity of said fluid on the core in order to connect a leading edge of the web to the core.

7. The method of claim 4, wherein said step of directing a fluid is carried out at a certain flow rate, and wherein said step of winding a length of the web is carried out at a certain speed, and including the step of varying the flow rate of fluid as the web is wound in accordance with the speed of winding the length of web about the wind-up spindle.

* * * * *